US008501938B2

(12) United States Patent
Malefyt et al.

(10) Patent No.: US 8,501,938 B2
(45) Date of Patent: *Aug. 6, 2013

(54) BENZOTHIAZOLE DERIVATIVES

(75) Inventors: Thomas R. Malefyt, Carmel Valley, CA (US); Leslie Pickford, South Francisco, CA (US)

(73) Assignee: Biotie Therapies, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/377,811

(22) PCT Filed: Jun. 16, 2010

(86) PCT No.: PCT/US2010/038868
§ 371 (c)(1),
(2), (4) Date: Dec. 12, 2011

(87) PCT Pub. No.: WO2010/148121
PCT Pub. Date: Dec. 23, 2010

(65) Prior Publication Data
US 2012/0083604 A1    Apr. 5, 2012

Related U.S. Application Data

(63) Continuation of application No. 12/486,457, filed on Jun. 17, 2009, now Pat. No. 8,168,785.

(51) Int. Cl.
C07D 413/14 (2006.01)
C07D 261/20 (2006.01)

(52) U.S. Cl.
USPC .......................................... 544/130; 546/198

(58) Field of Classification Search
USPC .......................................... 544/130; 546/198
See application file for complete search history.

(56) References Cited

U.S. PATENT DOCUMENTS

| | | | |
|---|---|---|---|
| 6,521,754 B2 | 2/2003 | Alanine et al. | |
| 7,368,446 B2 | 5/2008 | Flohr et al. | |
| 8,168,785 B2 * | 5/2012 | Malefyt et al. | 544/130 |
| 2008/0125419 A1 | 5/2008 | Alanine et al. | |

FOREIGN PATENT DOCUMENTS

| | | |
|---|---|---|
| EP | 1 753 760 B1 | 1/2008 |
| EP | 1 303 272 B1 | 2/2008 |
| WO | WO 01/97786 A2 | 12/2001 |
| WO | WO 03/053946 A1 | 7/2003 |
| WO | WO 2005/116026 A1 | 12/2005 |

OTHER PUBLICATIONS

European Examination Report, European Application No. 10728507.4, Nov. 8, 2012, 5 pages.
PCT Invitation to Pay Additional Fees, PCT/US2010/038868, Oct. 1, 2010, 6 pages.
PCT International Search Report and Written Opinion, PCT/US2010/038868, Dec. 8, 2010, 18 pages.
PCT International Preliminary Report on Patentability, PCT/US2010/038868, Jan. 5, 2012, 12 pages.

* cited by examiner

Primary Examiner — Rebecca Anderson
(74) Attorney, Agent, or Firm — Fenwick & West LLP

(57) ABSTRACT

Provided are compounds of formula I or II that are useful for the treatment of diseases related to the adenosine receptor. Also included are methods of treating patients suffering from or susceptible to at least one symptom of abuse of dependence on, or withdrawal from at least one substance.

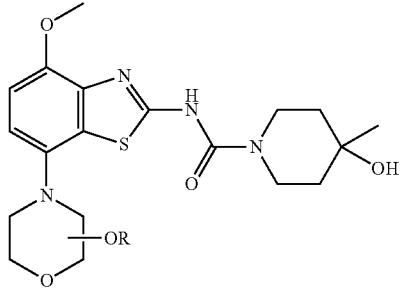

(I)

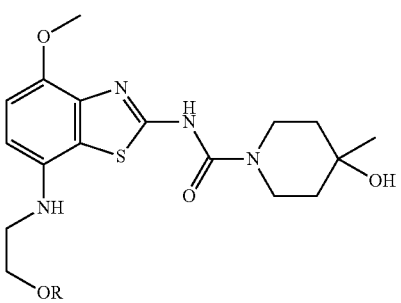

(II)

2 Claims, No Drawings

BENZOTHIAZOLE DERIVATIVES

CROSS-REFERENCE TO RELATED APPLICATIONS

This application is a 35 USC §371 national stage entry of PCT/US2010/038868, filed Jun. 16, 2010, and claims the benefit of U.S. application Ser. No. 12/486,457, filed on Jun. 17, 2009 which are hereby incorporated by reference in their entirety for all purposes.

FIELD OF THE INVENTION

The present invention is related to benzothiazole compounds, and more particularly to benzothiazole derivatives showing activity as adenosine receptor ligands.

BACKGROUND

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identity among the mammalian species. The $A_{2A}$ receptor (409-412 amino acids) was cloned from canine, rat, human, guinea pig and mouse, with a 93% homology of $A_{2A}$ receptor clone isolated from the human hippocampal library and from the dog. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes are to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmiters are ultimately responsible for neural degeneration and neural death, which causes brain damage or death of the individual. Adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2A}$-antagonists have therapeutic potential in the treatment of various forms of dementia, for example in Alzheimer's disease and are useful as neuroprotective agents. Adenosine $A_{2A}$-receptor antagonists inhibit the release of dopamine from central synaptic terminals and stimulate locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have therapeutic potential as sedatives, muscle relaxants, antipsychotics, anxiolytics, analgesics, respiratory stimulants and antidepressants, and they may be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonise the renal affects of adenosine, have potential as renal protective agents. Furthermore, adenosine $A_3$ and/or $A_{2B}$ antagonists may be useful in the treatment of asthma and other allergic responsesor and in the treament of diabetes mellitus and obesity.

SUMMARY

The present invention provides compounds containing the benzothiazole moiety, prodrugs of compounds containing the benzothiazole moiety, compositions comprising the compounds and prodrugs, and methods of using the compounds and prodrugs, including in the treatment and/or prevention of diseases mediated by the adenosine receptor.

The compounds of the invention have activity as adenosine receptor ligands. Accordingly, in still another aspect, the present invention provides methods of inhibiting the adenosine receptor comprising contacting an adenosine receptor with an effective amount of a compound or composition of the invention effective for inhibition. The methods can be practiced either in vitro or in vivo, and can be used as a therapeutic approach towards the treatment and/or prevention of diseases associated with the adenosine receptor.

In one aspect, the present invention provides compounds containing the benzothiazoleine moiety, and compositions comprising the compounds. The compounds have the general structures of formula I and II shown below:

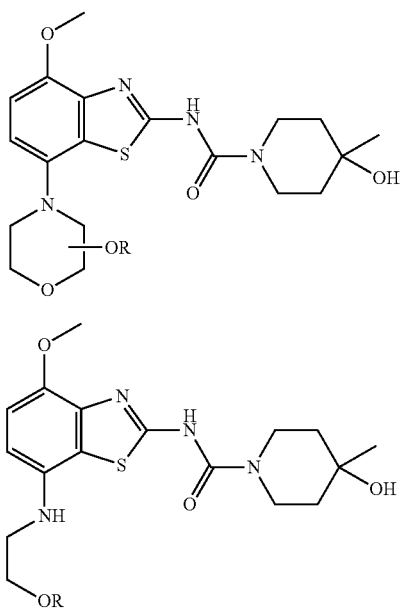

where R can be H or a progroup, $R^P$. The progroup $R^P$ is covalently attached via a carbamate, a thiocarbamate, a dithiocarbamate, a urea, or a thiourea linkage to oxygen atom. The compounds and compositions can be used in methods for the inhibition of A2a receptor.

Also provided are methods of treating at least one phase of cocaine dependence in a patient, in which the at least one phase is selected from acquisition, maintenance, extinction, and relapse. The methods include administering to the patient a therapeutically effective amount of the compound of the invention.

DETAILED DESCRIPTION

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

As used herein, the term "lower alkenyl" denotes a unsaturated straight- or branched-chain alkyl group containing from 2 to 6 carbon atoms, for example, ethylen, propylen, isopropylen, n-butylen, i-butylen, 2-butylen, t-butylen and the like. Preferred lower alkyl groups are groups with 2-4 carbon atoms.

The term "cycloalkyl" denotes a saturated carbocyclic group, containing 3-6 carbon atoms.

The term "halogen" denotes chlorine, iodine, fluorine and bromine.

"Haloalkyl," by itself or as part of another substituent, refers to an alkyl group as defined herein in which one or more of the hydrogen atoms is replaced with a halo group. The term "haloalkyl" is specifically meant to include monohaloalkyls, dihaloalkyls, trihaloalkyls, etc. up to perhaloalkyls. The halo groups substituting a haloalkyl can be the same, or they can be different. For example, the expression "($C_1$-$C_2$) haloalkyl" includes 1-fluoromethyl, 1-fluoro-2-chloroethyl, difluoromethyl, trifluoromethyl, 1-fluoroethyl, 1, 1-difluoroethyl, 1,2-difluoroethyl, 1,1,1-trifluoroethyl, perfluoroethyl, etc.

"Haloalkyloxy," by itself or as part of another substituent, refers to a group of the formula -O-haloalkyl, where haloalkyl is as defined herein.

The term "lower alkoxy" denotes a group wherein the alkyl residues are as defined above, and which is attached via an oxygen atom.

The term "five or six membered aromatic or non aromatic heterocycle" denotes the following group: aromatic heterocyclic groups are, for example pyrrol-1-yl, tetrazolyl, imidazol-1 or 2-yl, pyrazol1-yl, pyridin-1,2,3 or 4-yl, pyrazinyl, pyrimidinyl, pyridazinyl, isothiazolyl, isoxazolyl, thiazolyl, thienyl or furyl; Non aromatic heterocyclic groups are, for example, pyrrolidinyl, imidazolidinyl, pyrazolidinyl, piperidinyl, piperazinyl, morpholinyl, thiomorpholinyl, thiomorpholin-1,1-dioxo or thiomorpholin-1-oxo.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Pharmaceutically acceptable vehicle" refers to a diluent, adjuvant, excipient or carrier with which a compound of the invention is administered.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. The prodrug and active drug may have the same or different pharmacologic potency, selectivity or specificity, or a different pharmacological functionality. Prodrugs are typically obtained by masking a functional group in the drug believed to be in part required for activity with a progroup (defined below) to form a promoiety or "progroup" which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature, or combination thereof. The agent may be endogenous to the conditions of use, such as an enzyme present in, or secreted by, the cells to which the prodrug is administered or the acidic conditions of the stomach, or it may be supplied exogenously.

A wide variety of progroups suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active drug, converts the drug into a prodrug. Progroups are typically attached to the functional group of the drug via bonds that are cleavable under specified conditions of use.

The term "psychotic" as used herein refers to a psychiatric condition in its broadest sense, including hallucinations, a loss of ego boundaries, a gross impairment in reality testing, impairment with the capacity to meet ordinary demands of life, delusions, any prominent hallucinations, disorganized speech, or disorganized or catatonic behavior, and the like.

The term "psychosis" refers to a psychiatric symptom, condition or syndrome in its broadest sense, and can refer to a symptom associated with a general medical condition, a disease state or other condition, such as a side effect of drug abuse (a substance-induced disorder) or as a side effect of a medication. Psychosis includes a mental disorder or condition causing gross distortion or disorganization of a person's mental capacity, affective response, and capacity to recognize reality, communicate, and relate to others to the degree of interfering with his capacity to cope with the ordinary demands of everyday life.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

As used herein, the terms "treat" or "treatment" are used interchangeably and are meant to indicate a postponement of development of a disease and/or a reduction in the severity of such symptoms that will or are expected to develop, where the disease is associated with the functioning of a adenosine receptor. The terms further include ameliorating existing symptoms, preventing additional symptoms, and ameliorating or preventing the underlying metabolic causes of symptoms.

The compounds of the present invention may be used to inhibit or reduce the activity of A2a receptor. In these contexts, inhibition and reduction of activity of A2a receptor refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

The Compounds

As described in the Summary, the instant disclosure provides benzothiazoleine moiety containing compounds and their prodrugs of, such as the various benzothiazoleine compounds described in U.S. Pat. Nos. 6,521,754 and 7,368,446, EP 1 303 272, EP 1 753 760, and U.S. application Ser. No. 11/930,717 filed Oct. 31, 2007 (US2008/0125419). In particular, the compounds are of formula I and/or formula II:

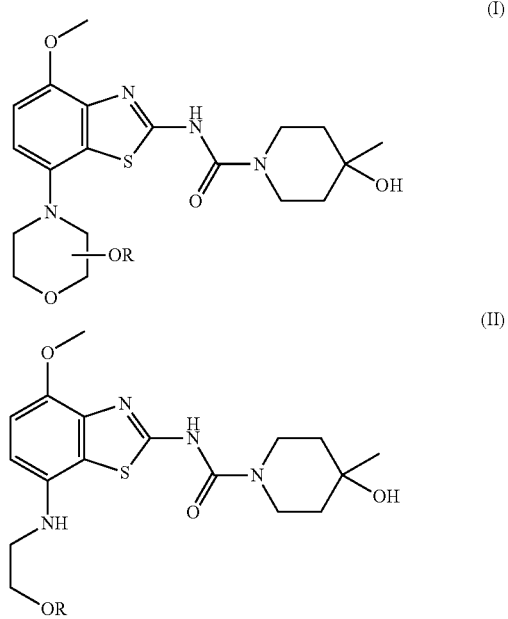

where R can be H or a progroup, $R^P$. The progroup $R^P$ can be covalently attached via a carbamate, a thiocarbamate, a dithiocarbamate, a urea, or a thiourea linkage to the oxygen atom. The compounds and compositions can be used in methods for the inhibition of A2a receptor.

The nature of the progroup can vary, and will depend upon, among other factors, the desired water solubility of the prodrug, its intended mode of administration and/or its intended mechanism or site of metabolism to the active benzothiazoleine compound. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, transport into the central nervous system (CNS), preventions or minimization of toxicity, etc. Groups capable of imparting prodrugs with these characteristics are well-known, and are described, for example, in Ettmayer et al. (2004) J. Med. Chem. 47:2393-2404. All of the various groups described in these references can be utilized in the prodrugs described herein.

The suitability of any particular progroup for a desired mode of administration can be confirmed in biochemical assays. For example, if a prodrug is to be administered by injection into a particular tissue or organ, and the identities of the various enzyme(s) expressed in the tissue or organ are known, the particular prodrug can be tested for metabolism in biochemical assays with the isolated enzyme(s). Alternatively, the particular prodrug can be tested for metabolism to the benzothiazoleine compound with tissue and/or organ extracts. Using tissue and/or organ extracts can be of particular convenience when the identity(ies) of the enzymes expressed in the target tissues or organs are unknown, or in instances when the isolated enzymes are not conveniently available. Skilled artisans will be able to readily select progroups having metabolic properties (such as kinetics) suitable for particular applications using such in vitro tests. The specific prodrugs could also be tested for suitable metabolism in in vitro animal models.

It has surprisingly been found that the compounds of formula I and II are adenosine receptor ligands.

The present invention, thus provides for the use of compounds of formula I and/or II or their pharmaceutically acceptable salts for the manufacture of medicaments for the treatment of diseases, related to the adenosine A2 receptor, their manufacture, medicaments based on a compound in accordance with the invention and their production as well as the use of compounds of formula I and/or II in the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents. The most preferred indications in accordance with the present invention are those, which base on the $A_{2A}$ receptor antagonistic activity and which include disorders of the central nervous system, for example the treatment or prevention of certain cognition impairment, sleep disorders, anxiety disorders especially generalized anxiety disorder (GAD), panic disorder, bipolar disorder, also known as manic depression or manic-depressive disorder, obsessive compulsive disorder (OCD), post-traumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease, Parkinson's disease, or psychosis, neuroprotection and Parkinson's disease as well as ADHD and diabetes mellitus. The compounds of formula I and/or II can be used for the treatment or prevention of addiction, such as cocaine addiction, nicotine addiction, cocaine addiction, alcohol and amphetamine addiction, and other chemical dependencies as well as movement disorders such as extrapyramidal syndrome, Tic disorders and restless leg syndrome (RLS).

The compounds of formulas I and II and their pharmaceutically usable addition salts possess valuable pharmacological properties. Specifically, it has been found that the compounds of the present invention can be adenosine receptor ligands and possess a high affinity towards the adenosine $A_{2A}$ receptor.

Methods of Synthesis

The compounds of the invention comprise benzothiazoleine moiety, as described above. The compounds can be obtained from commercial sources, such as Aldrich Chemical Co. (Milwaukee, Wis.), Sigma Chemical Co. (St. Louis, Mo.), or Maybridge (Cornwall, England), or the compounds can be synthesized. The compounds of the present invention, and other related compounds having different subtituents identified by any of the methods described above can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials useful for preparing compounds of the invention and intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995).

Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

All of the compounds were investigated in accordance with the test given hereinafter. Human adenosine $A_{2A}$ receptor The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^{3H}$]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

In accordance with the invention, it has been shown that all of the compounds of formula I and II have a high affinity toward the $A_{2A}$ receptor.

Uses and Administration

The compounds of formula I, formula II and the pharmaceutically acceptable salts of the compounds of formula I and formula Ia can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I and formula Ia can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I, formula II or a pharmaceutically acceptable salt thereof and a therapeutically inert carrier are also an object of the present invention, as is a process for their production, which comprises bringing one or more compounds of formula I and/or formal II and/or pharmaceutically acceptable acid addition salts and, if desired, one or more other therapeutically valuable substances into a galenical administration form together with one or more therapeutically inert carriers.

In accordance with the invention compounds of formula I and formula II as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure, substance abuse, sleep disorders and cognition disorders. Furthermore, compounds of the present invention may be useful as sedatives, muscle relaxants, antipsychotics, antiepileptics, anticonvulsants and cardioprotective agents and for the production of corresponding medicaments.

The most preferred indications in accordance with the present invention are those, which include disorders of the central nervous system, for example the treatment or prevention of certain depressive disorders, neuroprotection, Parkinson's disease, sleep disorders, cognitive impairment and motor disorders.

The dosage can vary within wide limits and will, of course, have to be adjusted to the individual requirements in each particular case. In the case of oral administration the dosage for adults can vary from about 0.01 mg to about 1000 mg per day of a compound of formula I, formula II or of the corresponding amount of a pharmaceutically acceptable salt thereof. The daily dosage may be administered as single dose or in divided doses and, in addition, the upper limit can also be exceeded when this is found to be indicated.

Treatment or Prevention of Substance Abuse

In one aspect of the invention, the compounds of formula I and/or II can be used for the treatment or prevention of substance abuse, and for modulating withdrawal symptoms. Withdrawal symptoms can arise upon reduction of any of a variety of substances. For example, the discontinued use of tobacco products, all of which contain nicotine, typically results in the onset of nicotine withdrawal conditions. Individuals often suffer the symptoms of nicotine withdrawal as a consequence of the discontinued use of tobacco in any form, including, but not limited to smoking of cigarette, cigar, or pipe tobacco, or the oral or intranasal ingestion of tobacco or chewing tobacco. Such oral or intranasal tobacco includes, but is not limited to snuff and chewing tobacco. The cessation of nicotine use or reduction in the amount of nicotine use, is often followed within 24 hours by symptoms including dysphoric, depressed mood; light-headedness; insomnia; irritability, frustration or anger; anxiety; nervous tremor; difficulty concentrating; restlessness; decreased heart rate; increased appetite or weight gain; and the craving for tobacco or nicotine. These symptoms often cause clinically significant distress or impairment in social, occupational, or other important areas of functioning. The methods described herein may be used to alleviate one or more symptoms attributed to nicotine withdrawal when such symptoms are not due to a general medical condition and are not better accounted for by another medical disorder. The present method is also helpful to those who have replaced, or partially replaced, their use of tobacco with the use of nicotine replacement therapy. Thus, such patients can be assisted to reduce and even eliminate entirely their dependence on nicotine in all forms.

The discontinuing or reduction in administration of an opioid, typically self-administration, through injection or orally, through smoking or intranasal ingestion, often results in the presence of a characteristic opioid withdrawal condition. This withdrawal condition can also be precipitated by administration of an opioid antagonist such as naloxone or naltrexone after opioid use. Opioid withdrawal is characterized by symptoms that are generally opposite to the opioid agonist effects. These withdrawal symptoms may include anxiety; restlessness; muscle aches, often in the back and legs; craving for opioids; irritability and increased sensitivity to pain; dysphoric mood; nausea or vomiting; lacrimation; rhinorrhoea; papillary dilation; piloerection; sweating; diarrhea; yawning; fever; and insomnia. When dependence is on short-acting opioids, such as heroin, withdrawal symptoms usually occur within 6-24 hours after the last dose, while with longer-acting opioids, such as methadone, symptoms may take 2-4 days to emerge. These symptoms often cause clinically significant distress or impairment in social, occupational or other important areas of functioning. The methods described herein can be used to alleviate one or more symptoms attributed to opioid withdrawal when such symptoms are not due to a general medical condition and are not better accounted for by another medical disorder.

The discontinuing of or reduction in use of ethanol (e.g., ethanol containing beverages) results in the onset of ethanol withdrawal conditions. Ethanol withdrawal conditions are characterized by symptoms that begin when blood concentrations of ethanol decline sharply, within 4 to 12 hours after ethanol use has been stopped or reduced. These ethanol withdrawal symptoms include craving for ethanol; autonomic hyperactivity (such as sweating or pulse rate greater than 100); hand tremor; insomnia; nausea; vomiting; transient visual, tactile, or auditory hallucinations or illusions; psychomotor agitation; anxiety; and grand mal seizures. These symptoms often cause clinically significant distress or impairment in social, occupational, or other important areas of functioning. The methods described herein may be used to alleviate one or more symptoms attributed to ethanol withdrawal when such symptoms are not due to a general medical condition and are not better accounted for by another medical disorder.

Cocaine abuse and dependence can cause cognitive, behavioral, and physiological symptoms. Symptoms of cocaine abuse and dependence can include varying degrees of attention deficit hyperactivity disorder and euphoria; increased energy, excitement, and sociability; less hunger and fatigue; a marked feeling of physical and mental strength; dysphoria; decreased sensation of pain; and craving for cocaine. Respiratory effects include symptoms such as bronchitis, shortness of breath, and chest pain, and cardiovascular effects include symptoms such as heart palpitations, arrhythmia, cardiomyopathy, and heart attacks. Symptoms also include dilated pupils, nausea, vomiting, headache, vertigo, anxiety, dizziness, psychosis, and confusion. Administration of cocaine through snorting or sniffing can result in ear, nose, and throat effects including nasal irritation, nasal crusting, recurrent nosebleeds, nasal stuffiness, and facial pain. In some embodiments, compounds of formula I and/or formula II treatment reduces at least one symptom of cocaine abuse and dependence in a patient. In some embodiments, nepicstat treatment increases at least one negative subjective symptom of cocaine abuse and dependence.

Cocaine withdrawal symptoms can include a fatigue, lack of pleasure, depression, irritability, sleep disorders, increased appetite, pyschomotor retardation, agitation, extreme suspicion, and craving for cocaine. In some embodiments, compounds of formula I and/or formula II treatment reduces at least one symptom of cocaine withdrawal.

Substance dependence can be characterized by the phases: acquisition, maintenance, extinction, and relapse. As used herein, the term "acquisition" refers to a phase of substance dependence in which dependence on the substance is initiated and acquired by a patient. In some embodiments, compounds of formula I and/or formula II treatment inhibits the development of the acquisition phase in a patient. In some embodiments, compounds of formula I and/or formula II treatment of the acquisition phase reduces at least one of the amount or frequency of substance use by a patient. In some embodiments, compounds of formula I and/or formula II treatment of the acquisition phase reduces at least one DSM-IV symptom of substance abuse and dependence in a patient. In some embodiments, compounds of formula I and/or formula II treatment of the acquisition phase reduces at least one symptom of substance abuse and dependence which include by way of example and without limitation at least one of euphoria, apathy, irritability, recklessness, poor judgment, compulsion, aggression, anger, craving for the substance being abused or depended upon, and mood disorders. In some embodiments, treatment with compounds of formula I and/or formula II reduces the substance craving induced by a stressful event in a patient during the acquisition phase.

"Maintenance" refers to a phase of substance dependence in which there is stable administration to or use of the substance by a patient. In some embodiments, a 10% variance in at least one of the amount and frequency of substance use by a patient is considered a stable behavior. In some embodiments, compounds of formula I and/or formula II treatment of the maintenance phase reduces at least one of the amount and frequency of substance use by a patient. In some embodiments, compounds of formula I and/or formula II treatment of the maintenance phase reduces at least one DSM-IV symptom of substance abuse and dependence in a patient. In some embodiments, compounds of formula I and/or formula II treatment of the maintenance phase reduces at least one symptom of substance abuse and dependence which includes by way of example and without limitation at least one of euphoria, apathy, irritability, recklessness, poor judgment, compulsion, aggression, anger, craving for the substance being abused or depended upon, and mood disorders. In some embodiments, treatment with compounds of formula I and/or formula II reduces the substance craving induced by a stressful event in a patient during the maintenance phase.

"Extinction" refers to a phase of substance dependence in which the substance is not provided to a patient or a patient abstains from use of the substance. In some embodiments, the dependence on the substance is extinguished or reduced in the extinction phase. In some embodiments, at least one withdrawal symptom occurs in the extinction phase. In some embodiments, compounds of formula I and/or formula II treatment promotes the development of the extinction phase in a patient. In some embodiments, compounds of formula I and/or formula II treatment of the extinction phase reduces at least one DSM-IV symptom of substance abuse and dependence in a patient. In some embodiments, compounds of formula I and/or formula II treatment during the extinction phase reduces at least one symptom of substance abuse and dependence which includes by way of example and without limitation at least one of euphoria, apathy, irritability, recklessness, poor judgment, compulsion, aggression, anger, craving for the substance being abused or depended upon, and mood disorders. In some embodiments, compounds of formula I and/or formula II treatment reduces the withdrawal symptoms in a patient in the extinction phase. In some embodiments, treatment with compounds of formula I and/or formula II reduces the substance craving induced by a stressful event in a patient in the extinction phase.

"Relapse" refers to recurrence of at least one symptom of substance abuse or dependence after a period of abstinence in a patient. In some embodiments, the relapse occurs at the end of remission. In some embodiments, a patient has undergone extinction training prior to relapse. In some embodiments, relapse occurs after drug priming, stress, or exposure to an environment related cue or stimulation that was previously associated with substance use. In some embodiments, compounds of formula I and/or formula II treatment reduces the frequency of relapse in a patient. In some embodiments, compounds of formula I and/or formula II treatment of the relapse phase reduces at least one DSM-IV symptom of substance abuse and dependence in a patient. In some embodiments, compounds of formula I and/or formula II treatment of the relapse phase reduces at least one symptom of substance abuse and dependence which includes by way of example and without limitation at least one of euphoria, apathy, irritability, recklessness, poor judgment, compulsion, aggression, anger, craving for the substance being abused or depended upon, and mood disorders. In some embodiments, compounds of formula I and/or formula II treatment reduces the withdrawal symptoms in a patient during the relapse phase. In some embodiments, treatment with compounds of formula I and/or formula II reduces the substance craving induced by a stressful event in a patient during the relapse phase.

Treatment of substance abuse, dependence, and withdrawal may be conducted in stages. In some embodiments, an initial period of abstinence from substance use is preferred before induction of treatment with compounds of formula I and/or formula II in a patient. In some embodiments, an initial low dose of compounds of formula I and/or formula II is administered to a patient. In some embodiments, the amount of compounds of formula I and/or formula II administered to a patient is escalated until a desired therapeutic response is observed. In some embodiments, the amount of compounds of formula I and/or formula II is escalated in order to determine the optimal dose to treat the condition while minimizing symptoms, side effects, and cravings for the substance in a patient.

In some embodiments, compounds of formula I and/or formula II treatment promotes remission. In some embodiments, the dose of compounds of formula I and/or formula II is unchanged or tapered off after remission is reached in a patient.

Provided are methods of treating a patient suffering from or susceptible to at least one symptom of abuse of, dependence on, or withdrawal from at least one substance. The methods include administering to the patient a therapeutically effective amount of compounds of formula I and/or formula II. In some embodiments, the at least one substance is selected from a drug of abuse and a medication. In some embodiments, the drug of abuse is selected from a psychostimulant agent, an opioid, a hallucinogen, an inhalant, a sedative, a tranquilizer, a hypnotic, an anxiolytic, and an illicit substance. In some embodiments, the psychostimulant agent is a beta-phenylisopropylamine derivative. In some embodiments, the beta-phenylisopropylamine derivative is selected from amphetamine, dextroamphetamine, and methamphetamine. In some embodiments, the psychostimulant agent is selected from ecstasy, phenmetrazine, methylphenidate, diethylpropion, pemoline, mazindol, (−) cathione, and fenfluramine. In some embodiments, the opioid is selected from Lortab, Tramadol, heroin, methadone, hydrocodone, and oxycodone. In some embodiments, the hallucinogen is selected from psilocybin, a hallucinogenic mushroom, lysergic acid diethylamide (LSD), phencyclidine (PCP), and ketamine. In some embodiments, the inhalant is selected from benzene, toluene, o-xylene, m-xylene, p-xylene, ethylbenzene, fluorobenzene, o-difluorobenzene, 1,3,5-triflurobenzene, 1,2,4-trifluorobenzene, pentafluorotoluene, pentafluorobenzene, and perfluorobenzene. In some embodiments, the medication is selected from an anesthetic, an analgesic, an anticholinergic agent, an antihistamine, a muscle relaxant, a nonsteroidal anti-inflammatory medication, an over the counter medication, and an antidepressant medication. In some embodiments, the drug of abuse is cocaine, alcohol, caffeine, opium, cannabinoid, cannabis, benzodiazapine carisprodol, tobacco, nicotine, Vicodin, Lorcet, Percocet, Percodan, and Tylox. In some embodiments, the drug of abuse is cocaine and compounds of formula I and/or formula II reduces at least one symptom of cocaine abuse and dependence in the patient selected from attention deficit hyperactivity disorder; euphoria; increased energy, excitement and sociability; less hunger and fatigue; a marked feeling of physical and mental strength; decreased sensation of pain; bronchitis; shortness of breath; chest pain; heart palpitations; arrhythmia; cardiomyopathy; heart attack; dilated pupils; nausea; vomiting; headache; vertigo; dizziness; anxiety; pychosis; confusion; nasal irritation; nasal crusting; recurrent nosebleeds; nasal stuffiness; facial pain; dysphoria; and craving for cocaine.

In some embodiments, the drug of abuse is cocaine and compounds of formula I and/or formula II increases at least one negative subjective symptom of cocaine abuse and dependence. In some embodiments, the drug of abuse is cocaine and compounds of formula I and/or formula II reduces at least one symptom of cocaine withdrawal selected from fatigue, lack of pleasure, depression, irritability, sleep disorders, increased appetite, pyschomotor retardation, agitation, extreme suspicion, and craving for cocaine. In some embodiments, compounds of formula I and/or formula II treatment improves a score of the patient on at least one of the attention deficit hyperactivity disorder IV rating scale (ADHD-IV), Hamilton Depression Scale (HAM-D), Hamilton Anxiety Scale (HAM-A), Beck Depression inventory (BDI), apathy scale from Neuropsychiatric Inventory, and a cognitive function rating scale. In some embodiments, the cognitive function rating scale is selected from the Wechsler Adult Intelligence Scale-Revised (WAIS-R), Wechsler Memory Scale-Revised (WMS-R), Rey Auditory Verbal Learning Test (RAVLT, Trials I-VII), Rey Complex Figure Test (RCFT), and the Trail Making Test (TMT, Parts A and B).

In some embodiments, compounds of formula I and/or formula II reduces in the patient at least one of the amount and frequency of substance use by the patient. In some embodiments, compounds of formula I and/or formula II reduces in the patient at least one symptom of abuse of, dependence on, or withdrawal from the at least one substance. In some embodiments, compounds of formula I and/or formula II reduces at least one symptom of substance abuse in the patient selected from recurrent substance use resulting in a failure to fulfill major role obligations at work, school, or home; recurrent substance use in situations in which it is physically hazardous; recurrent substance-related legal problems; and continued substance use despite having persistent or recurrent social or interpersonal problems caused or exacerbated by the effects of the substance. In some embodiments, compounds of formula I and/or formula II reduces at least one symptom of substance dependence in the patient selected from tolerance; withdrawal; the substance is often taken in larger amounts or over a longer period then was intended; there is a persistent desire and/or unsuccessful efforts to cut down or control substance use; a great deal of time is spent in at least one of activities to obtain the substance, use the substance, and recover from its effects; at least one of important social, occupational and recreational activities are given up and/or reduced because of substance use; and the substance use is continued despite knowledge of having a persistent and/or recurrent physical and/or psychological problem that is likely to have been caused or exacerbated by the substance.

In some embodiments, compounds of formula I and/or formula II promotes remission in the patient. In some embodiments, the remission is characterized by at least one of early full remission, early partial remission, sustained full remission, and sustained partial remission. In some embodiments, compounds of formula I and/or formula II prolongs a period of remission in the patient. In some embodiments, the methods further include treatment with at least one of contingency management and cognitive behavioral therapy.

In some embodiments, the methods further include co-administering a therapeutically effective amount of at least one other agent selected from a selective serotonin reuptake inhibitor (SSRI), a serotonin-norepinephrine reuptake inhibitor (SNRI), a norepinephrine reuptake inhibitor (NRI), a norepinephrine-dopamine reuptake inhibitor (NDRI), a serotonin 5-hydroxytryptamine1A (5HT1A) antagonist, a dopamine β-hydroxylase inhibitor, an adenosine receptor antagonist, an adenosine A2A receptor antagonist, a monoamine oxidase inhibitor (MAOI), a monoamine oxidase B inhibitor, a sodium channel blocker, a calcium channel blocker, a central and peripheral alpha adrenergic receptor antagonist, a central alpha adrenergic agonist, a central or peripheral beta adrenergic receptor antagonist, a NK-1 receptor antagonist, a corticotropin releasing factor (CRF) antagonist, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, a serotonin 5HT2 antagonist, an opioid, a carboxylase inhibitor, a partial opioid agonist, a partial nicotinic agonist, and an inhalant.

In some embodiments, the at least one other agent is a SSRI selected from paroxetine, sertraline, citalopram, escitalopram, and fluoxetine. In some embodiments, the at least one other agent is a SNRI selected from duloxetine, mirtazapine, and venlafaxine. In some embodiments, the at least one other agent is a NRI selected from bupropion and atomoxetine. In some embodiments, the at least other agent is the NDRI bupropion. In some embodiments, the at least one other agent is the dopamine β-hydroxylase inhibitor disulfiram. In some embodiments, the at least one other agent is the adenosine A2A receptor antagonist istradefylline. In some embodiments, the at least one other agent is a sodium channel blocker selected from lamotrigine, carbamazepine, oxcarbazepine, and valproate. In some embodiments, the at least one other agent is a calcium channel blocker selected from nimodopone, lamotrigine, and carbamazepine. In some embodiments, the at least one other agent is the central and peripheral alpha adrenergic receptor antagonist prazosin. In some embodiments, the at least one other agent is the central alpha adrenergic agonist clonidine. In some embodiments, the at least one other agent is the central or peripheral beta adrenergic receptor antagonist propranolol. In some embodiments, the at least one other agent is an atypical antidepressant/antipsychotic selected from bupropion, olanzepine, risperidone, and quetiapine. In some embodiments, the at least one other agent is a tricyclic selected from amitriptyline, amoxapine, desipramine, doxepin, imipramine, nortriptyline, protiptyline, and trimipramine. In some embodiments, the at least one other agent is an anticonvulsant selected from phenytoin, lamotrigine, carbamazepine, oxcarbazepine, valproate, topiramate, tiagabine, vigabatrin, and levetiracetam. In some embodiments, the at least one other agent is the glutamate antagonist topiramate. In some embodiments, the at least one other agent is a GABA agonist selected from baclofen, valproate, and topiramate. In some embodiments, the at least one other agent is the dopamine metabolism enzyme inhibitor carbidopa. In some embodiments, the at least one other agent is the partial dopamine D2 agonist aripiprazole. In some embodiments, the at least one other agent is an opioid receptor antagonist selected from naltrexone and naloxone. In some embodiments, the at least one other agent is a mood stabilizer selected from carbamazepine and lithium. In some embodiments, the at least one other agent is a direct or indirect dopamine agonist selected from dopamine, bromocriptine, pergolide, amantadine, mazindole, and methylphenidate. In some embodiments, the at least other agent is the partial 5HT1 agonist gepirone. In some embodiments, the at least other agent is the serotonin 5HT2 antagonist ritanserin. In some embodiments, the at least other agent is the opioid methadone. In some embodiments, the at least other agent is the partial opioid agonist buprenorphine. In some embodiments, the at least other agent is the partial nicotinic agonist champix. In some embodiments, the at least one other agent is an inhalant selected from benzene, toluene, o-xylene, m-xylene, p-xylene, ethylbenzene, fluorobenzene, o-difluorobenzene, 1,3,5-triflurobenzene, 1,2,4-trifluorobenzene, pentafluorotoluene, pentafluorobenzene, and perfluorobenzene. In some embodiments, the methods further include co-administering a therapeutically effective amount of least one other agent selected from benzodiazepine, levodopa, carisprodol, modafenil, acamprosate, gamma-butyrolactone, gamma-hydroxybutyrate, opium, psilopcybin, hallucinogenic mushroom, tobacco, and nicotine.

In some embodiments, compounds of formula I and/or formula II is administered to the patient after a period of abstinence from substance use by the patient. In some embodiments, the therapeutically effective amount of compounds of formula I and/or formula II in the patient is determined by escalating the amount of compounds of formula I and/or formula II administered to the patient until a desired therapeutic response is observed. In some embodiments, the amount of compounds of formula I and/or formula II is tapered off after remission is reached in the patient. In some embodiments, the amount of compounds of formula I and/or formula II is unchanged after remission is reached in the patient.

Also provided are methods of treating at least one phase of substance dependence on at least one substance in a patient. In some embodiments, the at least one phase of substance dependence is selected from acquisition, maintenance, extinction, and relapse. The methods include administering to the patient a therapeutically effective amount of compounds of formula I and/or formula II. In some embodiments, compounds of formula I and/or formula II inhibits the development of the acquisition phase in the patient. In some embodiments, compounds of formula I and/or formula II promotes the development of the extinction phase in the patient. In some embodiments, compounds of formula I and/or formula II reduces the frequency of relapse in the patient. In some embodiments, the at least one substance is selected from a drug of abuse and a medication. In some embodiments, the drug of abuse is selected from a psychostimulant agent, an opioid, a hallucinogen, an inhalant, a sedative, a tranquilizer, a hypnotic, an anxiolytic, and an illicit substance. In some embodiments, the psychostimulant agent is a beta-phenylisopropylamine derivative. In some embodiments, the beta-phenylisopropylamine derivative is selected from amphetamine, dextroamphetamine, and methamphetamine. In some embodiments, the psychostimulant agent is selected from ecstasy, phenmetrazine, methylphenidate, diethylpropion, pemoline, mazindol, (−) cathione, and fenfluramine. In some embodiments, the opioid is selected from Lortab, Tramadol, heroin, methadone, hydrocodone, and oxycodone. In some embodiments, the hallucinogen is selected from psilocybin, a hallucinogenic mushroom, lysergic acid diethylamide (LSD), phencyclidine (PCP), and ketamine. In some embodiments, the inhalant is selected from benzene, toluene, o-xylene, m-xylene, p-xylene, ethylbenzene, fluorobenzene, o-difluorobenzene, 1,3,5-triflurobenzene, 1,2,4-trifluorobenzene, pentafluorotoluene, pentafluorobenzene, and perfluorobenzene. In some embodiments, the medication is selected from an anesthetic, an analgesic, an anticholinergic agent, an antihistamine, a muscle relaxant, a nonsteroidal anti-inflammatory medication, an over the counter medication, and an antidepressant medication. In some embodiments, the drug of abuse is alcohol, caffeine, opium, cannabinoid, cannabis, benzodiazapine, carisprodol, tobacco, nicotine, Vicodin, Lorcet, Percocet, Percodan, and Tylox.

In some embodiments, compounds of formula I and/or formula II treatment improves a score of the patient on at least one of the ADHD-IV, HAM-D, HAM-A, BDI, apathy scale from Neuropsychiatric Inventory, and a cognitive function rating scale. In some embodiments, the cognitive function rating scale is selected from the WAIS-R, WMS-R, RAVLT, Trials I-VII, RCFT, and TMT, Parts A and B. In some embodiments, compounds of formula I and/or formula II reduces in the patient at least one of the amount and frequency of use of the at least one substance by the patient. In some embodiments, compounds of formula I and/or formula II reduces in the patient at least one symptom of abuse of, dependence on, or withdrawal from the at least one substance. In some embodiments, compounds of formula I and/or formula II reduces at least one symptom of substance abuse in the patient selected from recurrent substance use resulting in a failure to fulfill major role obligations at work, school, or home; recurrent substance use in situations in which it is physically hazardous; recurrent substance-related legal problems; and continued substance use despite having persistent or recurrent social or interpersonal problems caused or exacerbated by the effects of the substance. In some embodiments, compounds of formula I and/or formula II reduces at least one symptom of substance dependence in the patient selected from tolerance; withdrawal; the substance is often taken in larger amounts or over a longer period then was intended; there is a persistent desire and/or unsuccessful efforts to cut down or control substance use; a great deal of time is spent in at least one of activities to obtain the substance, use the substance, and recover from its effects; at least one of important social, occupational and recreational activities are given up and/or reduced because of substance use; and the substance use is continued despite knowledge of having a persistent and/or recurrent physical and/or psychological problem that is likely to have been caused or exacerbated by the substance.

In some embodiments, compounds of formula I and/or formula II promotes remission in the patient. In some embodiments, the remission is characterized by at least one of early full remission, early partial remission, sustained full remission, and sustained partial remission. In some embodiments, compounds of formula I and/or formula II prolongs a period of remission in the patient. In some embodiments, the methods further include treatment with at least one of contingency management and cognitive behavioral therapy.

In some embodiments, the methods further include co-administering a therapeutically effective amount of least one other agent selected from a selective serotonin reuptake inhibitor (SSRI), a serotonin-norepinephrine reuptake inhibitor (SNRI), a norepinephrine reuptake inhibitor (NRI), a norepinephrine-dopamine reuptake inhibitor (NDRI), a serotonin 5-hydroxytryptamine1A (5HT1A) antagonist, a dopamine β-hydroxylase inhibitor, an adenosine receptor antagonist, an adenosine A2A receptor antagonist, a monoamine oxidase inhibitor (MAOI), a monoamine oxidase B inhibitor, a sodium channel blocker, a calcium channel blocker, a central and peripheral alpha adrenergic receptor antagonist, a central alpha adrenergic agonist, a central or peripheral beta adrenergic receptor antagonist, a NK-1 receptor antagonist, a corticotropin releasing factor (CRF) antagonist, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, a serotonin 5HT2 antagonist, an opioid, a carboxylase inhibitor, a partial opioid agonist, a partial nicotinic agonist, and an inhalant. In some embodiments, the at least one other agent is a SSRI selected from paroxetine, sertraline, citalopram, escitalopram, and fluoxetine. In some embodiments, the at least one other agent is a SNRI selected from duloxetine, mirtazapine, and venlafaxine. In some embodiments, the at least one other agent is a NRI selected from bupropion and atomoxetine. In some embodiments, the at least other agent is the NDRI bupropion. In some embodiments, the at least one other agent is the dopamine β-hydroxylase inhibitor disulfiram. In some embodiments, the at least one other agent is the adenosine A2A receptor antagonist istradefylline. In some embodiments, the at least one other agent is a sodium channel blocker selected from lamotrigine, carbamazepine, oxcarbazepine, and valproate. In some embodiments, the at least one other agent is a calcium channel blocker selected from nimodopone, lamotrigine, and carbamazepine. In some embodiments, the at least one other agent is the central and peripheral alpha adrenergic receptor antagonist prazosin. In some embodiments, the at least one other agent is the central alpha adrenergic agonist clonidine. In some embodiments, the at least one other agent is the central or peripheral beta adrenergic receptor antagonist propranolol. In some embodiments, the at least one other agent is an atypical antidepressant/ antipsychotic selected from bupropion, olanzepine, risperidone, and quetiapine. In some embodiments, the at least one other agent is a tricyclic selected from amitriptyline, amoxapine, desipramine, doxepin, imipramine, nortriptyline, protiptyline, and trimipramine. In some embodiments, the at least one other agent is an anticonvulsant selected from phenytoin, lamotrigine, carbamazepine, oxcarbazepine, valproate, topiramate, tiagabine, vigabatrin, and levetiracetam. In some embodiments, the at least one other agent is the glutamate antagonist topiramate. In some embodiments, the at least one other agent is a GABA agonist selected from baclofen, valproate, and topiramate. In some embodiments, the at least one other agent is the dopamine metabolism enzyme inhibitor carbidopa. In some embodiments, the at least one other agent is the partial dopamine D2 agonist aripiprazole. In some embodiments, the at least one other agent is an opioid receptor antagonist selected from naltrexone and naloxone. In some embodiments, the at least one other agent is a mood stabilizer selected from carbamazepine and lithium. In some embodiments, the at least one other agent is a direct or indirect dopamine agonist selected from dopamine, bromocriptine, pergolide, amantadine, mazindole, and methylphenidate. In some embodiments, the at least other agent is the partial 5HT1 agonist gepirone. In some embodiments, the at least other agent is the serotonin 5HT2 antagonist ritanserin. In some embodiments, the at least other agent is the opioid methadone. In some embodiments, the at least other agent is the partial opioid agonist buprenorphine. In some embodiments, the at least other agent is the partial nicotinic agonist champix. In some embodiments, the at least one other agent is an inhalant selected from benzene, toluene, o-xylene, m-xylene, p-xylene, ethylbenzene, fluorobenzene, o-difluorobenzene, 1,3,5-triflurobenzene, 1,2,4-trifluorobenzene, pentafluorotoluene, pentafluorobenzene, and perfluorobenzene. In some embodiments, the methods further include co-administering a therapeutically effective amount of least one other agent selected from benzodiazepine, levodopa, carisprodol, modafenil, acamprosate, gamma-butyrolactone, gamma-hydroxybutyrate, opium, psilopcybin, hallucinogenic mushroom, tobacco, and nicotine.

In some embodiments, compounds of formula I and/or formula II is administered to the patient after a period of abstinence from substance use by the patient. In some embodiments, the therapeutically effective amount of compounds of formula I and/or formula II in the patient is determined by escalating the amount of compounds of formula I and/or formula II administered to the patient until a desired therapeutic response is observed. In some embodiments, the amount of compounds of formula I and/or formula II is tapered off after remission is reached in the patient. In some embodiments, the amount of compounds of formula I and/or formula II is unchanged after remission is reached in the patient.

Also provided are methods of treating at least one phase of cocaine dependence in a patient. In some embodiments, the at least one phase is selected from acquisition, maintenance, extinction, and relapse. The methods include administering to the patient a therapeutically effective amount of compounds of formula I and/or formula II. In some embodiments, compounds of formula I and/or formula II inhibits the development of the acquisition phase in the patient. In some embodiments, compounds of formula I and/or formula II promotes development of the extinction phase in the patient. In some embodiments, compounds of formula I and/or formula II reduces the frequency of relapse in the patient. In some embodiments, compounds of formula I and/or formula II reduces in the patient at least one symptom of abuse of, dependence on, or withdrawal from cocaine. In some embodiments, compounds of formula I and/or formula II reduces at least one symptom of cocaine abuse in the patient selected from recurrent cocaine use resulting in a failure to fulfill major role obligations at work, school, or home; recurrent cocaine use in situations in which it is physically hazardous; recurrent cocaine-related legal problems; and continued cocaine use despite having persistent or recurrent social or interpersonal problems caused or exacerbated by the effects of the cocaine. In some embodiments, compounds of formula I and/or formula II reduces at least one symptom of cocaine dependence in the patient selected from tolerance; withdrawal; the cocaine is often taken in larger amounts or over a longer period then was intended; there is a persistent desire or unsuccessful efforts to cut down or control cocaine use; a great deal of time is spent in activities to obtain the cocaine, use the cocaine, or recover from its effects; important social, occupational or recreational activities are given up or reduced because of cocaine use; and the cocaine use is continued despite knowledge of having a persistent or recurrent physical or psychological problem that is likely to have been caused or exacerbated by the cocaine. In some embodiments, compounds of formula I and/or formula II reduces at least one symptom of cocaine abuse and dependence selected from attention deficit hyperactivity disorder; euphoria; increased energy, excitement and sociability; less hunger and fatigue; a marked feeling of physical and mental strength; decreased sensation of pain; bronchitis; shortness of breath; chest pain; heart palpitations; arrhythmia; cardiomyopathy; heart attack; dilated pupils; nausea; vomiting; headache; vertigo; dizziness; anxiety; pychosis; confusion; nasal irritation; nasal crusting; recurrent nosebleeds; nasal stuffiness; facial pain; dysphoria; and craving for cocaine. In some embodiments, compounds of formula I and/or formula II increases at least one negative subjective symptom of cocaine abuse and dependence. In some embodiments, compounds of formula I and/or formula II reduces at least one symptom of cocaine withdrawal selected from fatigue, lack of pleasure, depression, irritability, sleep disorders, increased appetite, pyschomotor retardation, agitation, extreme suspicion, and craving for cocaine. In some embodiments, compounds of formula I and/or formula II improves a score of the patient on at least one of ADHD-IV, HAM-D, HAM-A, BDI, apathy scale from Neuropsychiatric Inventory, and a cognitive function rating scale. In some embodiments, the cognitive function rating scale is selected from WAIS-R, WMS-R, RAVLT, Trials I-VII, RCFT, and TMT, Parts A and B. In some embodiments, compounds of formula I and/or formula II reduces at least one of the amount and frequency of cocaine use by the patient. In some embodiments, compounds of formula I and/or formula II promotes remission in the patient.

In some embodiments, the remission is characterized by at least one of early full remission, early partial remission, sustained full remission, and sustained partial remission. In some embodiments, compounds of formula I and/or formula II prolongs a period of remission in the patient. In some embodiments, the methods further include treatment with at least one of contingency management and cognitive behavioral therapy.

In some embodiments, the methods further include co-administering a therapeutically effective amount of at least one other agent selected from a selective serotonin reuptake inhibitor (SSRI), a serotonin-norepinephrine reuptake inhibitor (SNRI), a norepinephrine reuptake inhibitor (NRI), a norepinephrine-dopamine reuptake inhibitor (NDRI), a serotonin 5-hydroxytryptamine1A (5HT1A) antagonist, a dopamine β-hydroxylase inhibitor, an adenosine receptor antagonist, an adenosine A2A receptor antagonist, a monoamine oxidase inhibitor (MAOI), a monoamine oxidase B inhibitor, a sodium channel blocker, a calcium channel blocker, a central and peripheral alpha adrenergic receptor antagonist, a central alpha adrenergic agonist, a central or peripheral beta adrenergic receptor antagonist, a NK-1 receptor antagonist, a corticotropin releasing factor (CRF) antagonist, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, a serotonin 5HT2 antagonist, an opioid, a carboxylase inhibitor, a partial opioid agonist, a partial nicotinic agonist, and an inhalant. In some embodiments, the at least one other agent is a SSRI selected from paroxetine, sertraline, citalopram, escitalopram, and fluoxetine. In some embodiments, the at least one other agent is a SNRI selected from duloxetine, mirtazapine, and venlafaxine. In some embodiments, the at least one other agent is a NRI selected from bupropion and atomoxetine. In some embodiments, the at least other agent is the NDRI bupropion. In some embodiments, the at least one other agent is the dopamine β-hydroxylase inhibitor disulfiram. In some embodiments, the at least one other agent is the adenosine A2A receptor antagonist istradefylline. In some embodiments, the at least one other agent is a sodium channel blocker selected from lamotrigine, carbamazepine, oxcarbazepine, and valproate. In some embodiments, the at least one other agent is a calcium channel blocker selected from nimodopone, lamotrigine, and carbamazepine. In some embodiments, the at least one other agent is the central and peripheral alpha adrenergic receptor antagonist prazosin. In some embodiments, the at least one other agent is the central alpha adrenergic agonist clonidine. In some embodiments, the at least one other agent is the central or peripheral beta adrenergic receptor antagonist propranolol. In some embodiments, the at least one other agent is an atypical antidepressant/antipsychotic selected from bupropion, olanzepine, risperidone, and quetiapine. In some embodiments, the at least one other agent is a tricyclic selected from amitriptyline, amoxapine, desipramine, doxepin, imipramine, nortriptyline, protiptyline, and trimipramine. In some embodiments, the at least one other agent is an anticonvulsant selected from phenytoin, lamotrigine, carbamazepine, oxcarbazepine, valproate, topiramate, tiagabine, vigabatrin, and levetiracetam. In some embodiments, the at least one other agent is the glutamate antagonist topiramate. In some embodiments, the at least one other agent is a GABA agonist selected from baclofen, valproate, and topiramate. In some embodiments, the at least one other agent is the dopamine metabolism enzyme inhibitor carbidopa. In some embodiments, the at least one other agent is the partial dopamine D2 agonist aripiprazole. In some embodiments, the at least one other agent is an opioid receptor antagonist selected from naltrexone and naloxone. In some embodiments, the at least one other agent is a mood stabilizer selected from carbamazepine and lithium. In some embodiments, the at least one other agent is a direct or indirect dopamine agonist selected from dopamine, bromocriptine, pergolide, amantadine, mazindole, and methylphenidate. In some embodiments, the at least other agent is the partial 5HT1 agonist gepirone. In some embodiments, the at least other agent is the serotonin 5HT2 antagonist ritanserin. In some embodiments, the at least other agent is the opioid methadone. In some embodiments, the at least other agent is the partial opioid agonist buprenorphine. In some embodiments, the at least other agent is the partial nicotinic agonist champix. In some embodiments, the at least one other agent is an inhalant selected from benzene, toluene, o-xylene, m-xylene, p-xylene, ethylbenzene, fluorobenzene, o-difluorobenzene, 1,3,5-triflurobenzene, 1,2,4-trifluorobenzene, pentafluorotoluene, pentafluorobenzene, and perfluorobenzene. In some embodiments, the methods further include co-administering a therapeutically effective amount of least one other agent selected from benzodiazepine, levodopa, carisprodol, modafenil, acamprosate, gamma-butyrolactone, gamma-hydroxybutyrate, opium, psilopcybin, hallucinogenic mushroom, tobacco, and nicotine. In some embodiments, compounds of formula I and/or formula II is administered to the patient after a period of abstinence from cocaine use by the patient. In some embodiments, the therapeutically effective amount of compounds of formula I and/or formula II in the patient is determined by escalating the amount of compounds of formula I and/or formula II administered to the patient until a desired therapeutic response is observed. In some embodiments, the amount of compounds of formula I and/or formula II is tapered off after remission from cocaine dependence is reached in the patient. In some embodiments, the amount of compounds of formula I and/or formula II is unchanged after remission from cocaine dependence is reached in the patient. In some embodiments, compounds of formula I and/or formula II treats at least one symptom of abuse of, dependence on, or withdrawal from at least one secondary substance in the patient. In some embodiments, the at least one secondary substance is selected from a drug of abuse and a medication. In some embodiments, the drug of abuse is selected from a psychostimulant agent, an opioid, a hallucinogen, an inhalant, a sedative, a tranquilizer, a hypnotic, an anxiolytic, and an illicit substance. In some embodiments, the psychostimulant agent is a beta-phenylisopropylamine derivative. In some embodiments, the beta-phenylisopropylamine derivative is selected from amphetamine, dextroamphetamine, and methamphetamine. In some embodiments, the psychostimulant agent is selected from ecstasy, phenmetrazine, methylphenidate, diethylpropion, pemoline, mazindol, (-) cathione, and fenfluramine. In some embodiments, the opioid is selected from Lortab, Tramadol, heroin, methadone, hydrocodone, and oxycodone. In some embodiments, the hallucinogen is selected from psilocybin, a hallucinogenic mushroom, lysergic acid diethylamide (LSD), phencyclidine (PCP), and ketamine. In some embodiments, the inhalant is selected from benzene, toluene, o-xylene, m-xylene, p-xylene, ethylbenzene, fluorobenzene, o-difluorobenzene, 1,3,5-triflurobenzene, 1,2,4-trifluorobenzene, pentafluorotoluene, pentafluorobenzene, and perfluorobenzene. In some embodiments, the medication is selected from an anesthetic, an analgesic, an anticholinergic agent, an antihistamine, a muscle relaxant, a nonsteroidal anti-inflammatory medication, an over the counter medication, and an antidepressant medication. In some embodiments, the drug of abuse is alcohol, caffeine, opium, cannabinoid, cannabis, benzodiazapine, carisprodol, tobacco, nicotine, Vicodin, Lorcet, Percocet, Percodan, and Tylox.

In another aspect of the invention, the methods include administering to the patient a therapeutically effective amount of compounds of formula I and/or formula II in combination with behavioral therapy including contingency management, cognitive behavioral therapy, motivational enhancement therapy, referral to self-help groups, and the like, for the treatment or prevention of drug use.

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

What is claimed is:

1. A compound of formula I, or a pharmaceutically acceptable salt thereof:

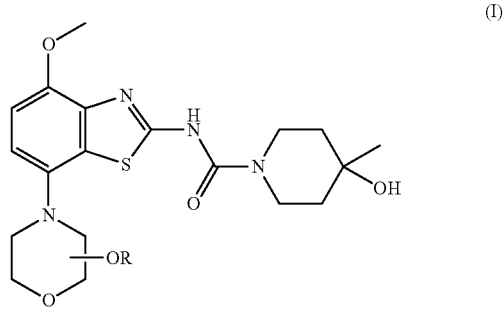

(I)

wherein R is H.

2. A compound of formula II, or a pharmaceutically acceptable salt thereof:

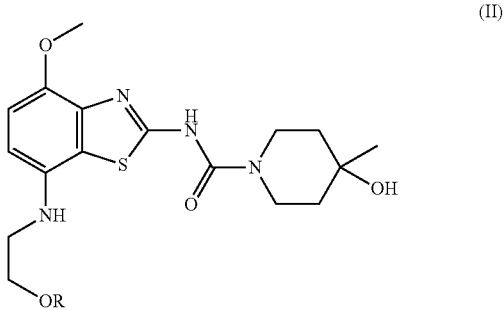

(II)

wherein R is H.

* * * * *

UNITED STATES PATENT AND TRADEMARK OFFICE
CERTIFICATE OF CORRECTION

| | | |
|---|---|---|
| PATENT NO. | : 8,501,938 B2 | Page 1 of 1 |
| APPLICATION NO. | : 13/377811 | |
| DATED | : August 6, 2013 | |
| INVENTOR(S) | : Thomas R. Malefyt et al. | |

It is certified that error appears in the above-identified patent and that said Letters Patent is hereby corrected as shown below:

On the title page

Item (57), Abstract section, line 3, in between "oftreating" please insert a space.

Item (57), Abstract section, line 4, after "of abuse of" insert --,-- and please insert a space before "dependence".

Signed and Sealed this
Fourth Day of March, 2014

Michelle K. Lee
*Deputy Director of the United States Patent and Trademark Office*